US00PP13595P39

(12) United States Plant Patent
Unger

(10) Patent No.: US PP13,595 P3
(45) Date of Patent: Feb. 25, 2003

(54) CUPHEA PLANT NAMED 'FIRECRACKER'

(76) Inventor: Michael Helmet Unger, Rheintalstrase 70, 79618 Rheinfelden (DE)

( * ) Notice: Subject to any disclaimer, the term of this patent is extended or adjusted under 35 U.S.C. 154(b) by 0 days.

(21) Appl. No.: 09/819,780

(22) Filed: Mar. 28, 2001

(65) Prior Publication Data

US 2002/0174465 P1 Nov. 21, 2002

(51) Int. Cl.[7] ..... A01H 5/00

(52) U.S. Cl. ..... Plt./226

(58) Field of Search ..... Plt./226

*Primary Examiner*—Bruce R. Campell
*Assistant Examiner*—Susan B. McCormick
(74) *Attorney, Agent, or Firm*—Wood, Phillips, Katz, Clark & Mortimer

(57) ABSTRACT

A new and distinct Cuphea plant named 'Firecracker', characterized by its vigorous trailing habit, dark red flowers with purple centers and dark green leaves.

2 Drawing Sheets

LATIN NAME OF THE GENUS AND SPECIES OF PLANT CLAIMED

*Cuphea hybrida.*

VARIETY DENOMINATION

'Firecracker'.

BACKGROUND OF THE INVENTION

The present invention comprises a new and distinct Cuphea plant, botanically known as *Cuphea hybrida* and hereinafter referred to by the cultivar name 'Firecracker'. The breeding program which resulted in the production of the new cultivar was carried out during 1999 at Rheinfelden, Germany. The female or seed parent of 'Firecracker' was an unnamed *Cuphea ilavea*. The male or pollen parent of 'Firecracker' was an unnamed *Cuphea purpurea*. The female (seed parent) is a tree-like tender perennial that has small red, blue and black flowers. The leaves are oval and shorter than the leaves of 'Firecracker'. The male (pollen parent) is more soft and herb-like that has flowers smaller than 'Firecracker'. The leaves are oval and shorter than the leaves of 'Firecracker'. The resulting seed was collected and germinated. 'Firecracker' was selected from flowering progeny.

Asexual reproduction of the new cultivar by terminal or stem cuttings taken during 2000 at West Chicago, Ill., USA has demonstrated that the characteristics of the new cultivar as herein described are firmly fixed and retained through successive generations of such asexual propagation.

SUMMARY OF THE INVENTION

It was found that the cultivar of the present invention:
(a) Exhibits a trailing habit,
(b) Forms red flowers with purple center, and
(c) Exhibits a vigorous growth habit.

'Firecracker' has not been observed under all possible environmental conditions to date. Accordingly, it is possible that the phenotype may vary somewhat with variations in the environment, such as temperature, light intensity and day length.

When the new cultivar of the present is compared to 'Tiny Mice' (not patented) it exhibits a more vigorous growth habit, smaller leaves, smaller petioles and slightly smaller petals as described in Table 1, below.

TABLE 1

| CHARACTERISTIC | 'FIRECRACKER' | 'TINY MICE' |
|---|---|---|
| PLANT HEIGHT - cm | 22.6 | 12 |
| LENGTH OF PLANT FROM TOP OF POT TO BOTTOM OF FOLIAGE - cm | 20 | 18 |
| LEAF LENGTH × WIDTH - cm | 5 × 1.5 | 5.9 × 1.7 |
| PETIOLE LENGTH × WIDTH - mm | 2.5 × .8 | 5 × 1.5 |
| PETAL LENGTH × WIDTH - cm | 1.5 × 1.5 | 1.2 × 1.2 |

BRIEF DESCRIPTION OF PHOTOGRAPHS

The accompanying photographs show as nearly true as it is reasonably possible to make the color illustrations of this type, typical flower and foliage characteristics of the new cultivar. The plants were grown for 12 weeks in a greenhouse at West Chicago, Ill., USA.

DETAILED BOTANICAL DESCRIPTION

Figure 1:
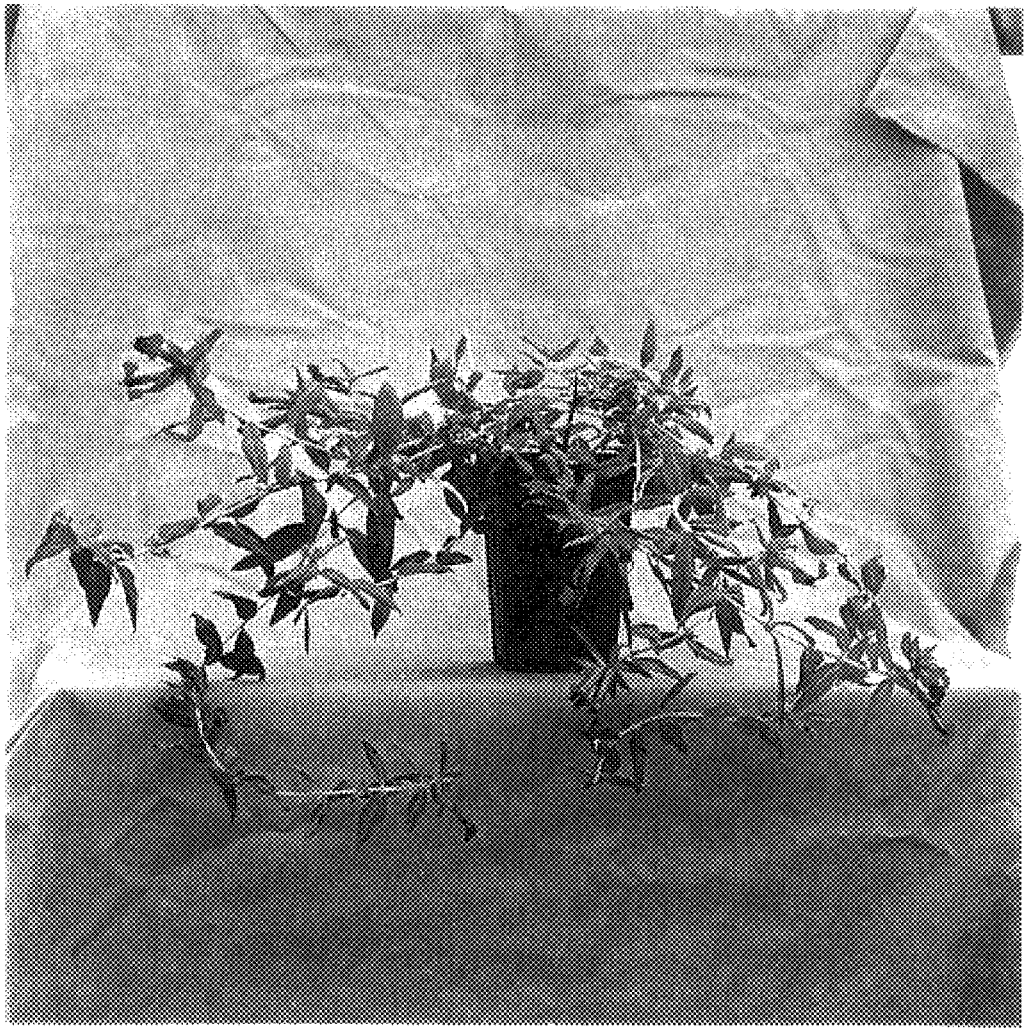
FIG. 1 illustrates the general growth habit of 'Firecracker'.
Figure 2:
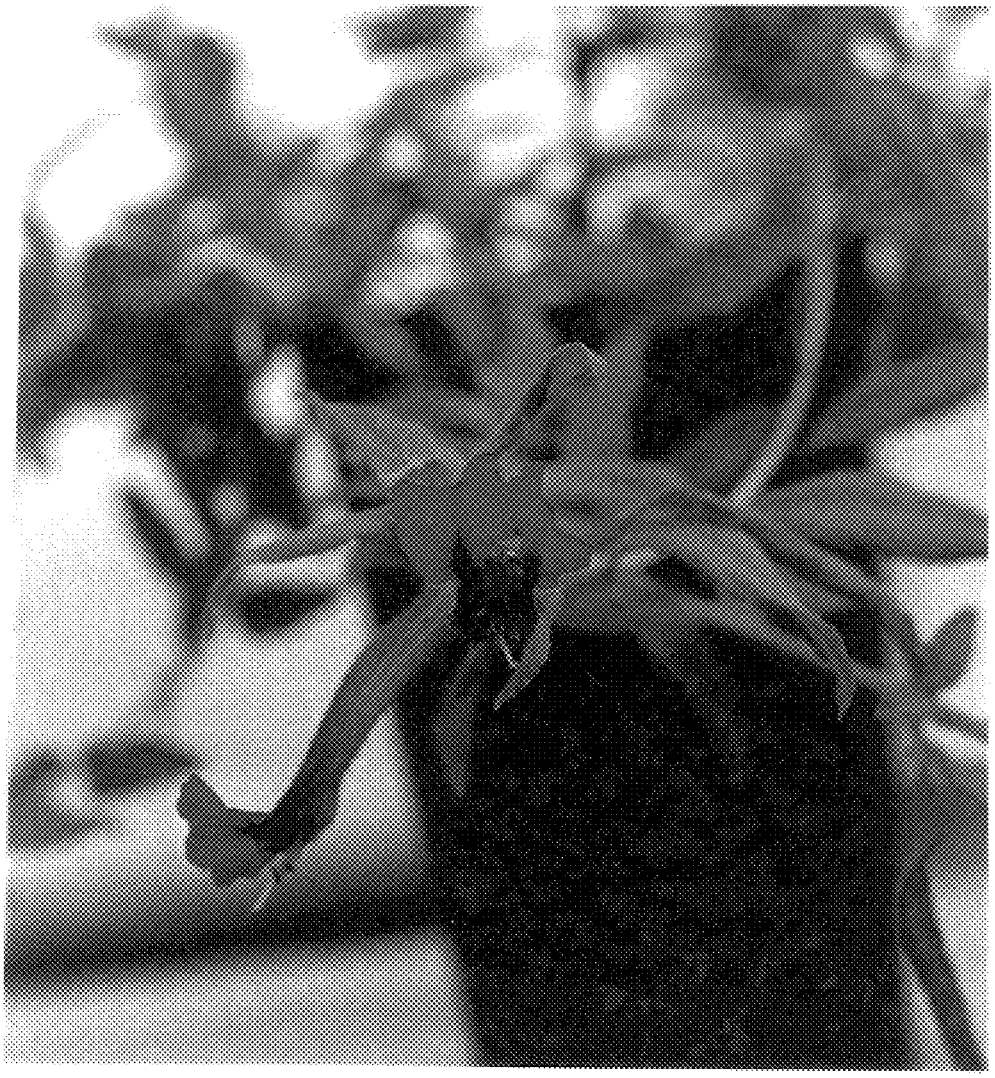
FIG. 2 illustrates individual flowers.

The chart used in the identification of colors described herein is The R.H.S. Colour Chart of The Royal Horticultural Society, London, England. The color values were determined on Mar. 6, 2001 in West Chicago, Ill. The readings were taken between 10:00 and 11:45 a.m. under natural daylight conditions. The plants were produced from cuttings taken from stock plants and were grown in a double polycarbonate covered greenhouse under conditions comparable to those used in commercial practice while utilizing a soiless growth medium and maintaining temperatures of approximately 72° F. during the day and approximately 65° during the night.

Botanical classification: *Cuphea hybrida* cultivar 'Firecracker'.

Propagation:

*Type cutting.*—Terminal tip.

*Time to initiate roots.*—Approximately 14–21 days with the shorter times generally being experienced in the summer and the longer times in the winter.

Plant description:

*General appearance and form.*—Trailing.

*Plant height above pot.*—Approximately 22.6 cm.

*Length of foliage from top of pot.*—Approximately 20 cm.

*Plant width.*—Approximately 39.8 cm.

*Branching habit.*—Freely branching. Pinching helps to initiate branching.

*Branch diameter.*—Approximately 2 mm.

*Stem.*—Surface: Densely covered with short hairs. Color: 145B.

Foliage description:

*Form.*—Simple.

*Shape.*—Lanceolate.

*Margin.*—Entire.

*Apex.*—Broadly acute.

*Base.*—Cuneate.

*Arrangement.*—Opposite.

*Venation pattern.*—Arcuate.

*Surface.*—Upper surface is rough. Sparsely covered with medium length stiff hairs; lower surface has rough hairs along veins.

*Color of mature foliage.*—Upper surface: Closest to 147A with veins of 145C.

*Color of mature foliage.*—Lower surface: Closest to 147B with veins of 145C.

*Size.*—Approximately 5 cm in length; approximately 1.5 cm in width.

*Petiole length.*—Approximately 2.5 mm.

*Petiole diameter.*—0.8 mm.

*Petiole color.*—144B.

Flower description:

*Outdoor flowering habit.*—'Firecracker' is freely flowering with substantially continuous blooming from spring until fall.

*Flower type.*—Solitary, axillary.

*Flower number per plant.*—Approximately 39.

*Flower number per cluster.*—An average of three.

*Flower size.*—Approximately 2 cm in diameter.

*Flower fragrance.*—None.

*Petal.*—Texture: Rugose. Shape: Obovate. Margin: Entire. Apex: Rounded. Length: Approximately 1.5 cm. Width: Approximately 1.5 cm.

*Petal color.*—Darker than 45A.

*Calyx tube.*—Surface: Hispid. Length: Approximately 3 cm. Diameter: Approximately 6 mm. Color: Closest to 145C with ribs of 144A.

*Reproductive organs.*—Androecium: 11. Stamens: 3 are 1 cm in length and smooth, 8 are 5 mm in length with matted hairs closest to 86A at distal end. Anthers are approximately 1.5 mm in length, closest to 86B in color. Pollen color is closest to 11D. Gynoecium: One pistil, approximately 4 cm in long. Stigma: Shape — round. Color — 87C. Style color: 150D with short stiff hairs of 86B at distil end. Ovary: Length — approximately 8 mm. Diameter — approximately 3 mm. Color — 150D.

Seed production: Seed production has not been observed.

Disease resistance: Resistance to pathogens has not been observed.

I claim:

1. A new and distinct cultivar of Cuphea plant named 'Firecracker' substantially as herein shown and described, which:

(a) Exhibits a trailing habit, (b) Forms dark red flowers with purple center, and (c) Exhibits a vigorous growth habit.

* * * * *